United States Patent
Dattner

(10) Patent No.: US 10,108,161 B2
(45) Date of Patent: Oct. 23, 2018

(54) SYSTEM AND METHOD FOR CONTROLLING AND MEASURING STEAM

(71) Applicant: AGAR Corporation Ltd., Grand Cayman (KY)

(72) Inventor: Yonathan Dattner, Calgary (CA)

(73) Assignee: AGAR CORPORATION LTD., Grand Cayman (KY)

(*) Notice: Subject to any disclaimer, the term of this patent is extended or adjusted under 35 U.S.C. 154(b) by 258 days.

(21) Appl. No.: 15/130,859

(22) Filed: Apr. 15, 2016

(65) Prior Publication Data

US 2016/0306367 A1    Oct. 20, 2016

Related U.S. Application Data

(60) Provisional application No. 62/148,936, filed on Apr. 17, 2015.

(51) Int. Cl.
| | |
|---|---|
| *G01N 15/02* | (2006.01) |
| *G05B 15/02* | (2006.01) |
| *G01N 21/45* | (2006.01) |
| *G01N 21/85* | (2006.01) |
| G01N 21/84 | (2006.01) |
| G01N 15/00 | (2006.01) |
| G01N 15/14 | (2006.01) |

(52) U.S. Cl.
CPC ......... *G05B 15/02* (2013.01); *G01N 15/0211* (2013.01); *G01N 21/45* (2013.01); *G01N 21/85* (2013.01); *G01N 15/1459* (2013.01); *G01N 2015/0026* (2013.01); *G01N 2021/8416* (2013.01)

(58) Field of Classification Search
None
See application file for complete search history.

(56) References Cited

U.S. PATENT DOCUMENTS

| | | | | |
|---|---|---|---|---|
| 4,137,462 A | * | 1/1979 | Wyler | G01N 21/534 250/227.11 |
| RE33,909 E | * | 5/1992 | Brenner | G01N 25/60 366/17 |
| 7,034,302 B2 | * | 4/2006 | Davidson | G01N 21/359 250/339.06 |
| 7,345,280 B2 | * | 3/2008 | Mitra | G01N 21/3504 250/345 |

(Continued)

*Primary Examiner* — Isaac T Tecklu
(74) *Attorney, Agent, or Firm* — Andrew W. Chu; Craft Chu PLLC

(57) ABSTRACT

A system and method for controlling steam based on a determination of steam quality include a steam conduit defining an interior volume of steam, an emitter for first and second coherent light beams, a receiver for signals resulting from an interference pattern of the first and second coherent light beams after refraction from a droplet in the steam at a convergence point, and a processor to determine steam quality based on the signals. There can be more than one receiver to account for phase differences related to droplet shape and size. The steam quality is also assessed by measuring droplet velocity by frequency of the interference patterns, and steam vapor and the refraction element of the scattering from the liquid droplet by absorption spectroscopy. The system can be utilized with on-line and real time measurements for on-line and real time determinations of steam quality.

33 Claims, 9 Drawing Sheets

(56) References Cited

U.S. PATENT DOCUMENTS

| | | | |
|---|---|---|---|
| 7,381,954 B2* | 6/2008 | Banerjee | G01N 21/3504 250/339.1 |
| 8,433,526 B2* | 4/2013 | Roy | G01N 15/0205 250/227.11 |
| 2004/0056197 A1* | 3/2004 | Davidson | G01N 21/359 250/339.1 |
| 2006/0053791 A1* | 3/2006 | Prentice, III | F23G 5/006 60/645 |
| 2007/0069131 A1* | 3/2007 | Banerjee | G01N 21/3504 250/339.1 |
| 2008/0231860 A1* | 9/2008 | Melnyk | G01F 1/7086 356/484 |
| 2012/0123696 A1* | 5/2012 | Roy | G01N 15/0205 702/24 |
| 2014/0224192 A1* | 8/2014 | Bool, III | F22B 1/1853 122/31.1 |
| 2014/0352423 A1* | 12/2014 | Kurz | G01F 1/684 73/204.11 |
| 2016/0266060 A1* | 9/2016 | Wiklund | G01N 27/223 |

* cited by examiner

SYSTEM AND METHOD FOR CONTROLLING AND MEASURING STEAM

CROSS-REFERENCE TO RELATED APPLICATIONS

The present application claims priority under 35 U.S.C. Section 119(e) from U.S. Provisional Patent Application Ser. No. 62/148,936, filed on 17 Apr. 2015, entitled "OPTICAL MONITORING, MEASUREMENT AND CONTROL OF STEAM QUALITY".

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to measuring and monitoring steam quality. In particular, the present invention relates to a system and method to detect water droplets in steam. Even more particularly, the present invention relates to optical measurement of water droplets in steam for adjustment of steam quality of the steam being produced.

2. Description of Related Art Including Information Disclosed Under 37 CFR 1.97 and 37 CFR 1.98.

Steam quality is defined as the proportion of saturated steam vapor in a liquid/vapor mixture. A steam quality of zero indicates 100% liquid, while a steam quality of one hundred percent indicates 100% steam vapor. Low steam quality affects steam system operations in several ways. In particular, low steam quality in heat transfer processes can reduce heat transfer efficiency by more than 65%. The liquid that is entrained in the steam has a significantly lower amount of energy than the steam vapor latent energy, and therefore low steam quality results in less usable energy being delivered to the steam process equipment. Further, the additional liquid that is present in the steam collects on wetted surfaces of the heat exchanger equipment, causing a buildup of liquid that reduces the ability of the heat exchanger to transfer the latent energy of the steam to a product. In addition, liquid passing through steam control valves can erode the internals of the valves, thereby contributing to premature valve failure. Similarly, the liquid that is introduced with the steam into a saturated turbine operation can reduce the life expectancy of the internal turbine components. Finally, since steam systems are not typically designed to accommodate the additional liquid that is present in low quality steam, the presence of the additional liquid increases the chance for a pressure surge, when a valve closes at the end of a pipeline, known as a water-hammer, to occur. Water-hammer is a safety issue and may cause premature failure in the steam system.

In other applications, such as thermally enhanced heavy oil recovery, steam is injected into the ground to lower the viscosity of the oil. Generated steam is required for the enhanced oil recovery process. The generated steam is monitored for steam quality because steam quality has an effect on the oil recovery process and efficiency. It is typical for a lower quality steam to be generated for enhanced oil recovery processes. Typically, treated re-used produced water is fed into the boiler. Due to the poor quality of the boiler-feed water (BFW), the maximum allowable steam quality to avoid boiler tube failure in Once through Steam Generators (OTSG) is only about 80%. On the other hand, drum boilers can operate at 100% steam quality but are only suitable for operation at much lower pressures than OTSG boilers, because at higher pressures they can experience tube deposition. The high-pressure conditions that are encountered during thermally enhanced heavy oil recovery operations often preclude the use of drum boilers. The generated steam for the enhanced oil recovery process must remain within a desirable range of steam quality. Steam quality can be monitored and controlled.

In current boiler operations the temperature, pressure and single-phase flow are measured and can be accurately derived. Unfortunately these readings do not give accurate quality measurements for the two-phase (vapor and liquid) steam coming out of the boiler, since 0% and 100% quality steam can have the same temperature and pressure. A throttling calorimeter is useful for certain steam quality measurements, but this method is not suitable for wet steam or for the high pressures that are used in the heavy oil industry.

Two methods are known for measuring steam quality online. The first uses a flow meter and Bernoulli's principle to calculate volumetric flow rates. This method is not accurate and has issues of working only for a short time due to clogging and deposition. The second online approach is based on mass flow calculations, and involves measuring the flow rate of the Boiler Feed Water (BFW) and then dividing the flow rate by the blow down flow rate. This latter method is also not accurate, and producers are having trouble getting the numbers to add up, likely because just measuring the blow down flow rate in the steam separator does not ensure ideal separation of the steam and liquid. Furthermore, this method does not give an indication of steam quality in each pass of the boiler.

Specific conductance measurement is a commonly used offline technique, which is based on the principle that the conductance of the water is proportional to the concentration of ions in the sample. When liquid boiler feed water is carried over in steam, the dissolved solids content of the boiler water contaminates the steam, and as a result the steam sample conductivity increases. A disadvantage of using specific conductance measurements is that some gases that are common to steam (such as carbon dioxide and ammonia) ionize in water solution. Even at extremely low concentrations, the ionized gases interfere with measurement of dissolved solids by increasing the conductivity.

Other known approaches for determining steam quality include optical monitoring methods, as taught in the following patents: U.S. Pat. No. 8,433,526, Method and system for steam quality monitoring; U.S. Pat. No. 7,381,954, Apparatus and method for measuring steam quality; U.S. Pat. No. 7,345,280, Measurement of steam quality using multiple broadband lasers; U.S. Pat. No. 7,034,302, Optical steam quality measurement system and method, and U.S. Pat. No. 4,137,462, Probe for measuring steam quality.

The prior art uses an emitter to send either a single wavelength or plural wavelengths of light through a steam conduit to a receiver, the emitter and the receiver being directly lined up one with the other. In each of the methods the intensity of light that is incident on the receiver is related back to steam quality, and various approaches of sending wavelengths that are more and less sensitive to liquid and vapor water are used to extract information via the Beer-Lambert law. For instance, U.S. Pat. No. 8,433,526 discloses a method for determining droplet size using a lined up emitter/receiver configuration, in which the intensity of light that is incident on the receiver when a dry steam is measured is compared to the intensity of light that is incident on the receiver when a wet steam is measured. The droplet size is determined based on the intensity drop measured at the receiver, and is related to total scattering based on Mie Scattering theory.

FIGS. 1A and 1B illustrate three types of scattering from a liquid droplet in a steam conduit. In particular, FIG. 1A illustrates scattering due to diffraction 3 when a beam of light 1 interacts with a water droplet 2, and FIG. 1B illustrates scattering due to reflection 6A and scattering due to refraction 7 when a beam of light 4A interacts with a water droplet 5. It is important to note that scattering due to diffraction and reflection contain no absorptive information relating to the liquid droplet, and that only scattering due to refraction contains absorptive information. A closed solution for the scattering of a plane wave from a spherical, homogeneous, isotropic particle (in this case a spherical water droplet) was first presented by Lorenz in 1890 and by Mie in 1908, which is known as the Lorenz-Mie Theory (LMT). The LMT solution is documented in the literature by Born M., Wolf E "Principles of Optics" Cambridge University Press London, Born M. "Optik" Springe, Verlag Berlin 1981, Kerker D M. "The Scattering of Light" Academic Press, New York, London 1969 and Boheren C F, Huffman D R "Absorption and Scattering of Light by Small Particles" Wiley 2007. An extension using the Debye series was also documented by Debye in 1908 and Hovenac E A, Lock J A "Assessing the contribution of surface waves and complex rays to far field Mie Scattering by use of Debye Series" Journal of Optical Society America, Volume 9, pp. 781-795, 1992, which allows the computed scattered field to be interpreted in terms of scattering orders.

FIG. 2 presents a summary of the intensity distribution of the first 10 scattering orders of water droplets in air, as calculated using LMT and Debye Series. Diffraction dominates the signal that is detected at the receiver with a scattering angle of zero, i.e. when the receiver is lined up directly with the emitter. A contribution due to refraction is present at zero degrees scattering angle, but it is two orders of magnitude lower than the diffraction contribution. For this reason, the perceived loss of optical power at the receiver is dominated by diffraction at zero degrees scattering angle.

The diffraction of a homogenous wave from a spherical droplet can be approximated using Fraunhofer diffraction from a circular disc. The Intensity $I(\theta)_{Diff}$ due to diffraction at a point on a lined up emitter/receiver is given by equation (1):

$$I(\theta)_{Diff} \propto \left[\frac{J_1\left(\pi D \sin\left(\frac{\theta}{\lambda}\right)\right)}{\pi D \sin\left(\frac{\theta}{\lambda}\right)}\right]^2 \quad (1)$$

Where $J_1$ is the Bessel Function of the first kind of order one, D is the diameter of the droplet and $\theta$ is the convergence angle. So when multiple wavelengths, some of which are more sensitive to absorption in liquid compared to vapor and vice versa, are sent through a steam conduit in a lined-up emitter/receiver configuration, all wavelengths will experience a large intensity drop due to diffraction and the wavelengths which are more sensitive to absorption in liquid will experience a much smaller change compared to the wavelengths which are not sensitive to absorption in liquid. With decreasing steam quality the intensity drop becomes increasingly large, due to the larger size of the water droplets and/or due to the larger number of water droplets present in the steam, which places a lower limit on the steam quality that can be measured using a lined-up emitter/receiver configuration. This can be seen in the published results of J. K. Partin, J. R. Davidson (Idaho National Laboratory August 2006), where the optical signal was near zero for 99.4% steam quality by mass.

It would be beneficial to provide a system and method that overcomes at least some of the above-mentioned limitations.

It is an object of the present invention to provide an embodiment of a measurement system to collect absorptivity information relating to liquid water droplets entrained in steam in steam system operations.

It is another objection of the present invention to provide an embodiment of an online optical monitoring and measurement system to derive water vapor content, as well as the velocity, directional velocity, shape and size of liquid water droplets entrained in steam in steam system operations.

These and other objectives and advantages of the present invention will become apparent from a reading of the attached specification.

BRIEF SUMMARY OF THE INVENTION

Embodiments of the invention are directed to systems for the optical-based monitoring, measurement and control of steam quality and associated methods that substantially overcome one or more of the problems due to the limitations and disadvantages of the prior art.

At least one of the above and other features and advantages may be realized by providing a monitoring, measurement and control system in which, in its simplest form, two beams of coherent light of a single frequency (wavelength) intersect in a measurement volume with a beam intersection angle $\Theta$. Two detectors placed at off-axis angle $\varphi$ and elevation angles $\pm\Psi$ are positioned to receive light from the two beams of coherent light after propagation through the measurement volume. The design of such a system is based on the principle that, for given illumination waves and detector positions, each scattering order, e.g. reflection or refraction, leaves the droplet surface at its respective glare point and traverses a unique path to each detector. In the case of two illumination waves, at least two glare points exist for each scattering order. These glare points can be viewed as coherent light sources directed towards the detectors, which produce interference fringes in the far field. The interference fringes move in space according to particle (i.e., water droplet) movement through the illuminating waves, and also according to which scattering order is being considered. The fringe movement or the frequency of modulation measured on a detector yields water droplet velocity. Thus, two detectors each detect a modulated signal as the interference fringes cross the respective apertures; however, a phase shift results due to the spatial separation of the detectors. The phase shift can be related to the spatial fringe spacing and to the distance between glare points on the particle surface through the geometric parameters of the optical system. The measured phase from one detector and for one scattering order can be related to the droplet shape and size. The droplet size is related to steam quality through conversion of the volumetric parameters with respect to pressure, temperature of the system to total mass of water liquid and water vapor preset in the steam conduit.

Placement of the two detectors may be such that first order refraction dominates the resulting signal. In particular, placement of the two detectors may be at off-axis angles from ~10 degrees to ~60 degrees such that first order refraction dominates by at least two orders of magnitude. The interference fringe frequency may be related to droplet velocity, and relative phase difference may be related to droplet shape. There also exists an absorption coefficient in the refractive measurement, but the coefficient is difficult to calculate with single wavelength operation. The coefficient may be predicted based on comparison to the reflection scattering mode, which does not contain absorptive information. In an embodiment, the system may use an additional wavelength and the absorption contribution may be derived with more accuracy.

With single wavelength operation, there exists a directional velocity ambiguity, which may be solved by introducing a small frequency shift to one of the two beams of coherent light.

Additionally, there exists a $2\pi$ ambiguity when using two detectors, which limits the maximum droplet size that can be determined. In an embodiment a third detector is utilized to support the measurement of larger droplet sizes.

In an alternative embodiment, the $2\pi$ ambiguity limiting the maximum droplet size determination that is achievable with a two-detector configuration is overcome by performing additional software analysis, which analyzes the time shift of the detected signals with increasing droplet size.

In an alternative embodiment, a hardware solution to overcome the $2\pi$ ambiguity limiting the maximum droplet size determination that is achievable with a two-detector configuration is to include at least a third detector. With three detectors, three phase differences are measured for each droplet. Due to the different elevation angles, the phase difference/diameter relations for the three detectors pairs are different. Two of the three phase differences can be used for two independent particle diameter estimations while the third measurement can be used as validation criteria, because the sum over all phase differences must vanish.

In an alternative embodiment, a dual mode configuration in which two detectors are placed at off-axis angle $\varphi$ and elevation angles $\pm\Psi$, and two detectors are placed on an equatorial line of the droplet in the plane of the incident beams, is employed. This configuration is referred to as a planar configuration. In such a dual mode configuration the system exhibits a much lower sensitivity to droplet size and can be used to overcome the $2\pi$ ambiguity of maximum droplet size, but care must be taken when the droplet sizes being measured are small.

In an alternative embodiment, a reference beam configuration in which two detectors are placed at the off-axis angle of $\pm\varphi=\Theta/2$ and elevation angle of $\Psi=0$, is employed. This configuration may exhibit a much larger droplet diameter resolution but additional detectors need to be incorporated to overcome the $2\pi$ ambiguity of maximum droplet size.

In an alternative embodiment, instead of using one wavelength of light, multiple discrete wavelengths are used, e.g. using common multiplexing techniques such as time division multiplexing of the individual wavelengths. The detectors that are employed in this alternative embodiment must have detection capabilities for each of the discrete wavelengths used. According to this alternative embodiment, absorption spectroscopy techniques can be applied, in which wavelengths with different absorption characteristics to water vapor and water liquid can be used.

It is a feature of an embodiment of the invention to employ radiation in the optical measurement having a wavelength within the range from about 1100 nm to about 2500 nm, with a resolution of about 1 nm. The intensity of the light source is controlled to be constant over time.

Embodiments of the invention also include utilizing the above systems and associated methods for controlling the steam quality flowing in a steam conduit. Various approaches may be used to control steam quality, depending on where the steam quality is being measured. For instance, on a steam turbine heat is added to the steam generator, blow down is controlled and/or flow rates are controlled.

According to an aspect of at least one embodiment, there is provided a system for measuring and controlling steam quality of steam within a steam conduit, the system comprising: a steam conduit comprising a conduit wall defining an internal volume for containing steam in a steam system; an emitter for launching first and second coherent light beams toward a convergence point within the internal volume; a receiver for receiving a signal resulting from interference in space of light from the first and second coherent light beams after refraction from a droplet in the steam at the convergence point, the receiver comprising an output port for providing an output signal based on the received signal; a processing portion in communication with the receiver for receiving the output signal therefrom, and comprising a processor determining a steam quality value of the steam in the conduit based on the output signal, and for determining a control signal based on the determined steam quality value; a controller in communication with the processor for adjusting a parameter of the steam system based on the control signal; and a feedback path being disposed in communication between the processing portion and the controller for providing the control signal from the processing portion to the controller.

According to an aspect of at least one embodiment, there is provided a system for measuring and controlling steam quality of steam within a steam conduit, the system comprising: a steam conduit comprising a conduit wall defining an internal volume for containing steam in a steam system; an optical sensor portion mounted on the steam conduit and comprising: an emitter for launching first and second coherent light beams through the internal volume and along respective first and second optical paths that converge with a convergence angle $\theta$, each optical path forming an angle $\theta/2$ with an optical axis of the emitter; and a receiver comprising at least two receiving elements, each of the at least two receiving elements being in communication with a photosensitive element, the at least two receiving elements located off the optical axis of the emitter and at respective positions along the conduit wall for receiving a signal resulting from interference in space of light from the first and second coherent light beams after refraction from a droplet in the steam, the respective positions of the at least two receiving elements being such that each receiving element receives the signal with a different phase, and the receiver further comprising an output port for providing an output signal based on the signal received by the at least two receiving elements; a processing portion in communication with the receiver for receiving the output signal therefrom, and comprising a processor for determining a steam quality value of the steam based on the output signal and for providing a control signal based on the determined steam quality; a controller in communication with the processor for adjusting a parameter of the steam system based on the control signal; and a feedback path being disposed in communication between the processing portion and the controller for providing the control signal from the processing portion to the controller.

According to an aspect of at least one embodiment, there is provided a method for measuring and controlling steam quality of steam within a steam conduit, the method comprising: providing a flow of steam within a steam conduit of a steam system; using an emitter, directing first and second coherent light beams toward a convergence point within the internal volume; detecting an optical signal incident on each one of a plurality of photosensitive elements and providing an output signal based on said detecting, the optical signal resulting from interference in space of refracted light from the first and second coherent light beams after refraction from a droplet in the steam at the convergence point, determining a control signal based on the output signal, the control signal for controlling a parameter of the steam system; providing the control signal to a controller of the steam system via a feedback communication path; and using the controller, controlling the parameter of the steam system so as to alter a property of the flow of steam within the steam conduit.

DETAILED DESCRIPTION OF THE INVENTION

Figure 1A:
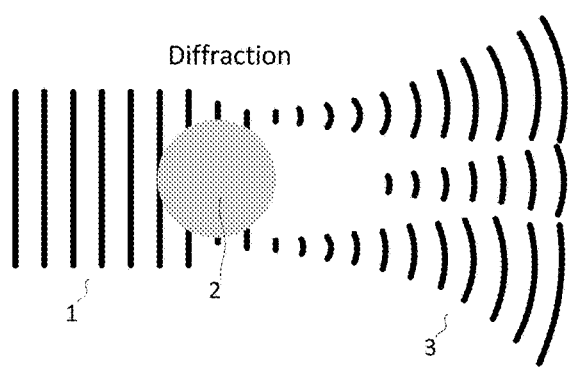
FIG. 1A is a schematic view, illustrating scattering from a droplet of water due to diffraction.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein.

In the following description and in the appended claims, the following terms and symbols are to be accorded the following definitions:

A "steam conduit" denotes a conduit, a pipeline, a downhole or a chamber serving to pass or contain steam.

An "emitter" denotes a system, assembly or collection of components including an emitting element that is a source of electromagnetic radiation. The term "emitter" is not limited to the emitting element itself, but also refers to associated system components including but not limited to optical fibers, lenses, windows, packaging, etc.

A "receiver" denotes a system, assembly or collection of components including a photosensitive element that converts received electromagnetic radiation into a signal that can be interpreted. The term "receiver" is not limited to the photosensitive element itself, but also refers to associated system components including but not limited to optical fibers, lenses, windows, packaging, etc. A receiving element may be disposed for receiving the electromagnetic radiation and for passing the received electromagnetic radiation on to a photosensitive element that is disposed some distance away.

Steam flow is understood to be in the x-direction.

Intersection angle is $\Theta$ (mirrored about the y-z plane).

Off-Axis angle is $\varphi$ (measured from the x-z plane).

Elevation angle is $\psi$ (measured from the y-z plane).

$\varphi_r$ is the reference phase, i.e. phase obtained on a detector when the water droplet is at the center of the measurement volume.

"Measurement volume" is referred to as the "Phase Reference Plane." This is where the particle position and time-independent phase is zero, i.e. ($\varphi_r(x=0)=0$ deg).

$\Delta\varphi_{(x,y)}$ is the phase difference between detector x and detector y.

Complex Refractive index is n*.

Real part of refractive index is n.

The area where a coherent light beam first interacts with a water droplet is referred to as the "incident point" and the source area of the scattered wave is referred to as the "glare point."

A "steam system" is a system utilizing steam in an intended process, such as an industrial process like an enhanced oil recovery process. The steam system adjust a parameter of the steam system, according to the steam quality determined by the present invention. For example, on a steam turbine as a steam system, heat is added to the steam generator of the steam turbine, blow down is controlled and/or flow rates are controlled.

Unless explicitly stated or implied, the use of the singular form of a word is intended to also include the plural form of the word, and vice versa.

Figure 1B:
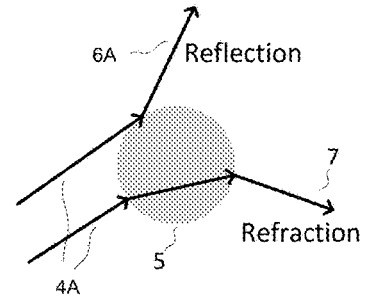
FIG. 1B is a schematic view, illustrating scattering from a droplet of water due to reflection and refraction.

FIGS. 1A and 1B illustrate the three types of scattering effects that occur when an optical (i.e., coherent light) beam 1, 4A impinges on a droplet of liquid (i.e., a water droplet) 2, 5 in a steam turbine or other environment. The first scattering type shown in FIG. 1A is diffraction 3. From equation (1) it is apparent that for spherical waves and a homogenous wave the intensity of light that is received at a receiver, at a scattering angle of zero, decreases as the droplet size increases. The radiation that is scattered by diffraction does not hold any absorptive information about the liquid droplet, and diffraction is the dominant scattering effect when an emitter is lined up with a receiver, as is the case in all of the approaches that are currently in use. In all current approaches the intensity decrease that is measured at the receiver is related to steam quality, and it is assumed either that droplet size increases or that more droplets are present in the beam path with lower steam quality. The main problem with such assumptions is that droplet shape may vary under different process conditions, such as pressure, temperature and flow rate, while the steam quality remains constant, thereby producing false results. In FIG. 1B the two other scattering effects are shown, namely reflection 6A and refraction 7. Refraction 7 is important for the analysis of steam quality because as a light beam passes through a liquid droplet the light is partially absorbed, depending on the imaginary parts of the refractive index of the liquid droplet. The angles of reflection and refraction are dependent on the real part of the refractive index and Snell's law. The refractive index n* of water, either liquid or vapor, can be expressed as shown in equation (2), where n is the real part of the refractive index and k is the imaginary part. Both the real and imaginary parts of the refractive index are dependent on temperature and wavelength. The imaginary part of the refractive index can be related to the molar absorptivity of the water, and utilizing the Beer-Lambert Law the intensity loss due to refraction in the droplet can be derived from measurements and related to droplet size.

$$n^* = n(T,\lambda) + ik(T,\lambda) \qquad (2)$$

Figure 2:
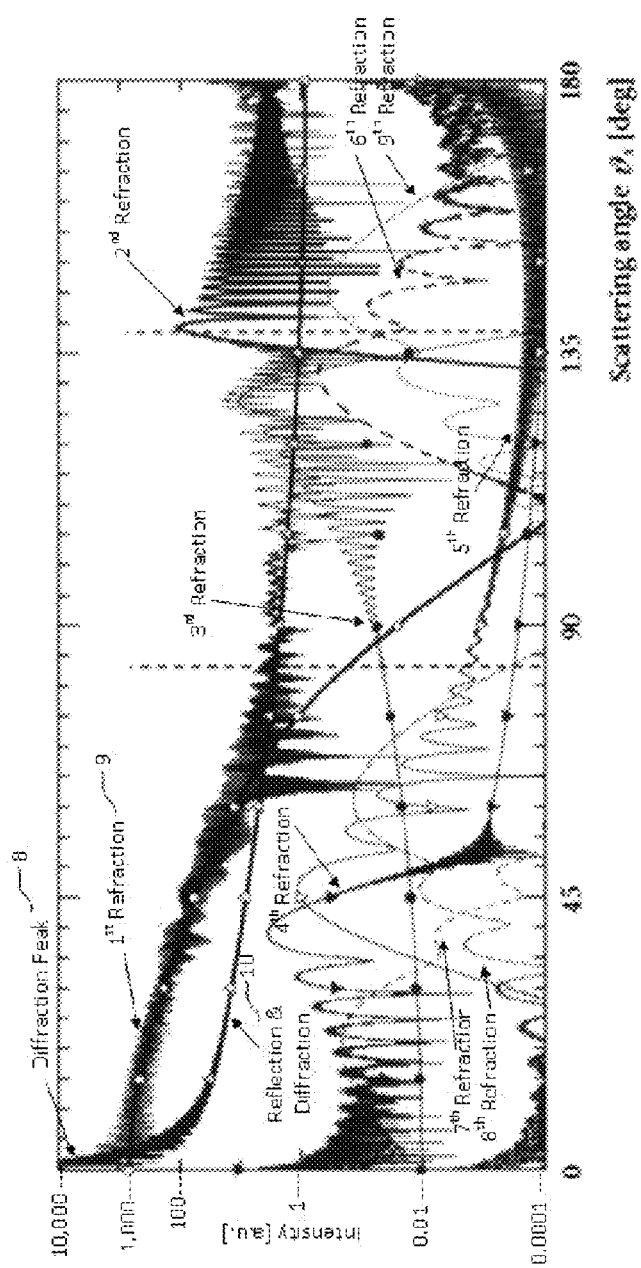
FIG. 2 illustrates the intensity distribution of the first 10 scattering orders as a function of scattering angle for a water droplet, calculated using Lorenz-Mie Theory (LMT) and Debye Series Decomposition.

Referring now to FIG. 2, shown is the intensity distribution of the first 10 scattering orders as a function of scattering angle for a water droplet, as calculated according to Lorentz-Mie Theory (LMT) and Debye Series Decomposition. As expected, if the emitter and receiver are lined up, i.e. zero scattering angle, then the dominant contribution to the intensity at the receiver is due to diffraction 8. As is also shown in FIG. 2, diffraction is one order of magnitude higher than refraction, the diffraction peak being at intensity of 10,000 [a.u.] for zero scattering angle while first order refraction 9 is at intensity of 1,000 [a.u.] for zero scattering angle. Since diffraction does not hold absorptive information about the liquid droplet, i.e. the receiver cannot collect any data about the absorption of light by the liquid droplet with respect to the imaginary part of equation (2), it is therefore preferable to place the receiver at an angle at which refraction is dominant. As shown in FIG. 2, at scattering angles between 10 degrees and 60 degrees the first order refraction 9 is dominant, while diffraction and reflection 10 are much lower contributors. Higher order refraction $X^{th}$, where X is the refraction order, is the number of times the illuminating wave gets reflected internally to the water droplet before leaving the water droplet and propagating towards the receiver, thereby being absorbed more and more as it propagates back and forth within the water droplet. Every higher refraction order (m) has a $\pi$ phase shift relative to its respective one-order lower (m−1) refraction order due to reflection at the water droplet inner surface.

Figure 3A:
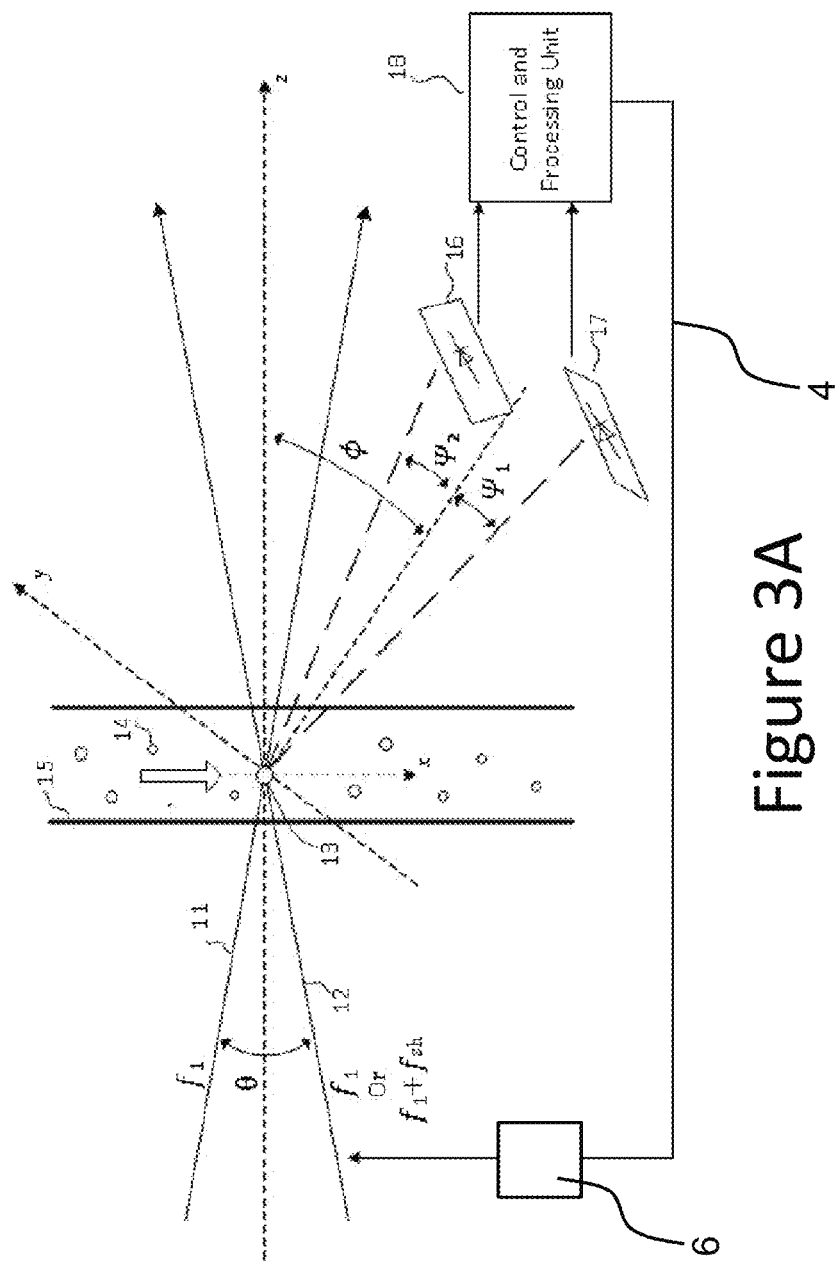
FIG. 3A is a simplified diagram illustrating a dual beam optical system for measuring steam quality in a steam conduit utilizing Laser Doppler Velecomietery and Phase Doppler Anemometry techniques in a two-detector configuration.
Figure 3B:
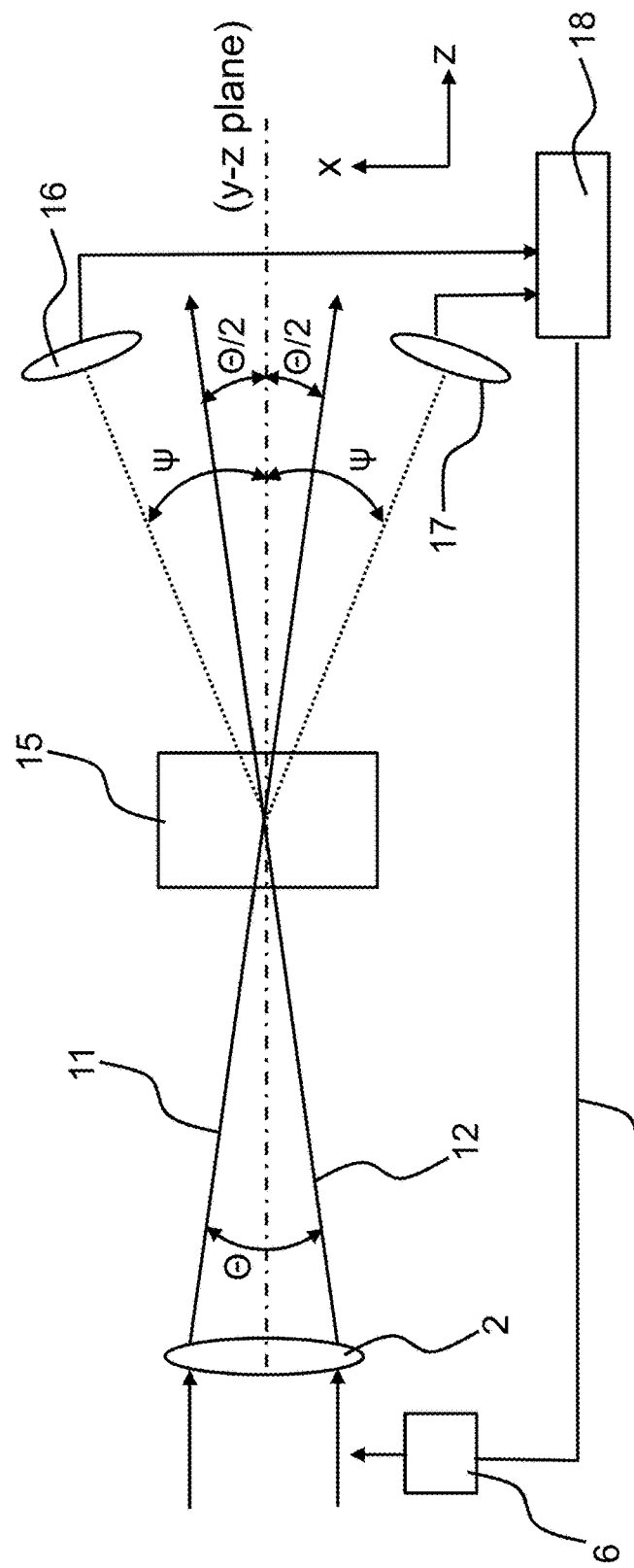
FIG. 3B is a simplified side-view of the system shown in FIG. 3A.
Figure 3C:
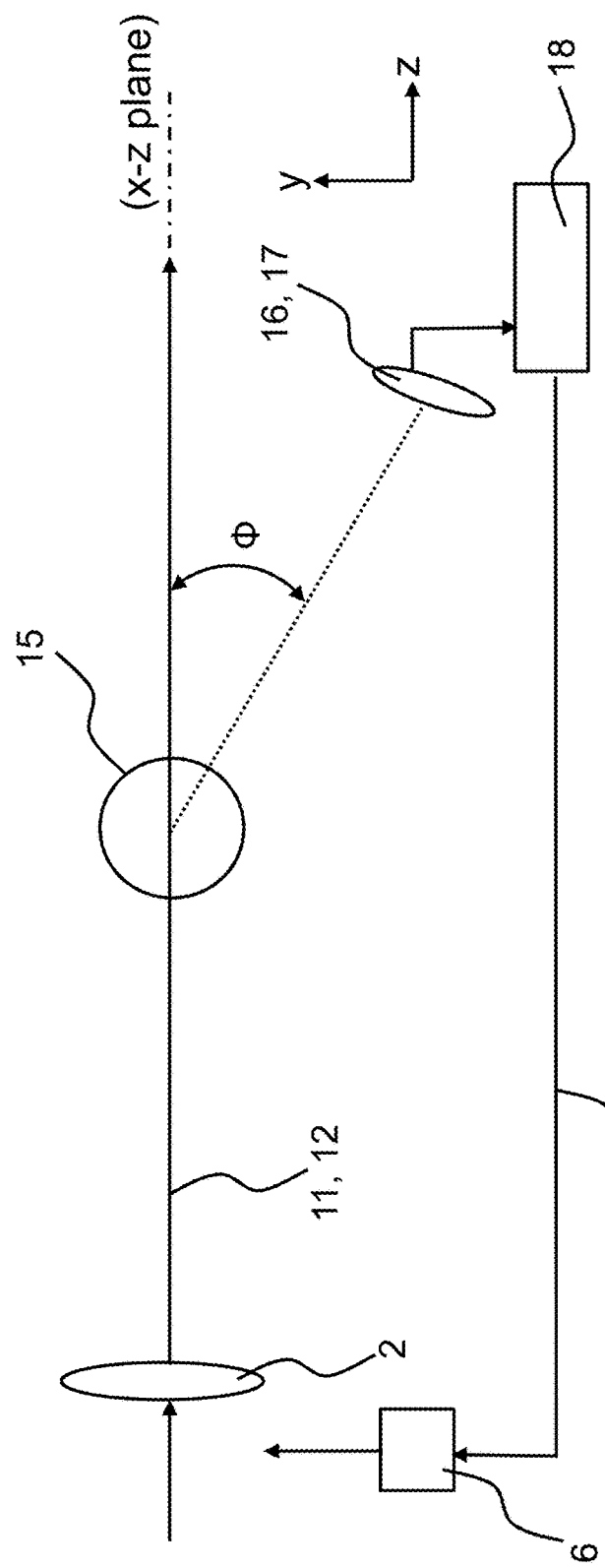
FIG. 3C is a simplified top-view of the system shown in FIG. 3A.

FIG. 3A is a simplified diagram showing a system according to an embodiment, the system having a two-detector configuration and employing Phase Doppler Anemometry (PDA) and Laser Doppler Velocimetry (LDV) techniques. FIGS. 3B and 3C show simplified side and top views, respectively, of the system of FIG. 3A. Non-saturated steam flows in a steam conduit 15 having a conduit wall, and droplets of water liquid 14 are present in the steam. An emitter shown generally at 2 in FIGS. 3B and 3C launches two coherent light beams 11, 12, with the same polarization of the same frequency $\lambda_1 = f_1$, and which converge on measurement volume 13 with an intersection angle of Θ. Optionally, one of the two coherent light beams 11, 12 has a frequency shift $f_{sh}$ relative to the other. The detected droplet position and time-dependent phase appear as a constant phase offset at each detector 16, 17. For spherical droplets the measured phase for first order refraction, where $\varphi_{r1}$ and $\varphi_{r2}$ is the reference phase for detector 16 and 17, respectively, is given by equations (3) and (4):

$$\varphi_{r1} = \frac{2\pi}{\lambda_1} d_d \left( \sqrt{n_d(T,\lambda_1)\sqrt{2} \sqrt{\frac{1 + n_d^2(T,\lambda_1) - }{\frac{1 + \sin\psi_1 \sin\Theta/2 + }{\cos\psi_1 \cos\emptyset \cos\Theta/2}}}} - \sqrt{n_d(T,\lambda_1)\sqrt{2} \sqrt{\frac{1 + n_d^2(T,\lambda_1) - }{\frac{1 - \sin\psi_1 \sin\Theta/2 + }{\cos\psi_1 \cos\emptyset \cos\Theta/2}}}} \right) \qquad (3)$$

$$\varphi_{r2} = \frac{2\pi}{\lambda_1} d_d \left( \sqrt{n_d(T,\lambda_1)\sqrt{2} \sqrt{\frac{1 + n_d^2(T,\lambda_1) - }{\frac{1 + \sin\psi_2 \sin\Theta/2 + }{\cos\psi_2 \cos\emptyset \cos\Theta/2}}}} - \sqrt{n_d(T,\lambda_1)\sqrt{2} \sqrt{\frac{1 + n_d^2(T,\lambda_1) - }{\frac{1 - \sin\psi_2 \sin\Theta/2 + }{\cos\psi_2 \cos\emptyset \cos\Theta/2}}}} \right) \qquad (4)$$

Where $\lambda_1$ is the wavelength of the beam and is related to frequency through $$f_1 = \frac{c}{\lambda_1 n_d(T,\lambda_1)}$$

in which $n_d(T,\lambda_1)$ is the refractive index of the water droplet, which is also dependent on temperature T and wavelength $\lambda_1$, c is the speed of light in vacuum, $d_d$ is the water droplet diameter and the angular distributions are shown in FIG. 3.

To convert the phase difference to droplet diameters the phase conversion factor for spherical droplets and symmetrically aligned detectors, i.e. $|\Psi_1|=|\Psi_2|$, will be denoted as $F_\phi$. For first order refraction $F_\phi$ is given by equation (5):

$$F_\phi = \frac{\lambda_1}{2\pi} \left[ 2 \left( \sqrt{\frac{1 + n_d^2(T,\lambda_1) - n_d(T,\lambda_1)\sqrt{2}\sqrt{\frac{1 + \sin\psi_2 \sin\Theta/2 + \cos\psi_2 \cos\varnothing \cos\Theta/2}{\cos\psi_2 \cos\varnothing \cos\Theta/2}}}{1 + n_d^2(T,\lambda_1) - n_d(T,\lambda_1)\sqrt{2}\sqrt{\frac{1 - \sin\psi_2 \sin\Theta/2 + \cos\psi_2 \cos\varnothing \cos\Theta/2}{\cos\psi_2 \cos\varnothing \cos\Theta/2}}}} \right)^{-1} \right] \quad (5)$$

The droplet diameter $d_d$ is thereby derived in the Control and Processing Unit (CPU) 18 by taking the phase difference (3), (4) and relating it to the phase conversion factor for first order refraction and spherical droplets of water in equation (6), where $\Delta\varphi_{r,12}$ is the phase difference seen in the interference patterns on the two detectors 16, 17 at a given time:

$$d_d = |\varphi_{r1} - \varphi_{r1}| \times |F_\phi| = |\Delta\varphi_{r,12}| \times |F_\phi| \quad (6)$$

From equation (6) for a two-detector configuration it is evident that there exists a $2\pi$ ambiguity once the droplet size reaches a certain diameter. For first order refraction the maximum droplet diameter for a two-detector configuration is given by equation (7), where $\Psi_1 = -\Psi_2 = \Psi_{1,2}$;

$$d_{dmax} = 2\pi F_\phi \quad (7)$$

$$\approx \frac{\lambda_1 |\cos\varnothing/2| \sqrt{1 + n_d^2(T,\lambda_1) - 2n_d(T,\lambda_1)|\cos\varnothing/2|}}{n_d(T,\lambda_1)\psi_{1,2}\varnothing/2}$$

To derive the droplet velocity in the direction of steam propagation (x direction), the frequency of the interference fringes seen on the detector is measured. The amplitude of the interference fringes modulate with a frequency $f_d$, which refers to the difference between the two Doppler shifted waves of the two incident beams 11, 12 on the droplet. The droplet velocity $v_{dx}$ in the x-direction is given by equation (8):

$$v_{dx} = \frac{f_d \lambda_1}{2\sin\varnothing/2} \quad (8)$$

Two droplets moving in opposite directions through the measurement volume 13 generate the same interference fringe frequency per equation (8). Therefore, to recover directional information an optional frequency shift $f_{sh}$ may be introduced to one of the beams 12 of coherent light, causing the interference modulation to either increase by $f_{sh}$ if the droplet is moving against the fringes or decrease by $f_{sh}$ if the droplet is moving with the fringes.

The CPU 18 shown in FIG. 3A includes the optical components, mechanical components, hardware, software, etc., for carrying out the monitoring, measurement and control functions of the system. On the emitting side the CPU 18 includes an emitter (shown at 2 in FIGS. 3B and 3C) including an emitting element, which may be provided in the form of an in-line probe which houses the optics, lasers, light source, and electronics required to emit the beams of coherent light 11, 12. The emitter includes the optical components such as lenses, beam splitters, Bragg cells, fiber optics, and emitting element such as lasers, light emitting diodes, superluminescent Light Emitting Diodes, broad band sources and supercontinuum sources, etc. Feedback control to the emitting element is also applied via feedback path 4 and controller 6, such that constant optical intensity is achieved over time. To isolate the components from the steam within the steam conduit 15, a not illustrated window made of Sapphire or diamond can be used to allow the beams of coherent light 11, 12 to enter the measurement volume 13. The emitter assembly or parts thereof may be actively heated to prevent any condensate from forming on the not illustrated window. Additional techniques such as using ultra-sonic pulsing additionally or alternatively are employed to remove solids that become deposited on the not illustrated window.

On the receiving side the CPU 18 includes a receiver including a photosensitive element (shown generally at 16 and 17 in FIGS. 3B and 3C), which may similarly be provided in the form of an in-line probe with not illustrated sapphire or diamond windows, and similar methods such as actively heating and ultra-sonic pulsing may be used to prevent and/or remove condensation or solids that become deposited on the not illustrated windows. The receiver may include fiber optics, photodiode detectors, electronic, analog circuitry for photodiode readout, Analog to digital converts, digital signal processing, central processing unit, memory and communication hardware and protocols. Based on the measured data, the CPU 18 sends control signals via feedback path 4 and controller 6 to a not illustrated steam generation unit for controlling the steam quality, e.g. such as by controlling at least one parameter of the steam generation unit based on the control signals.

Optionally, the CPU 18 includes software for processing the measured data to overcome the $2\pi$ ambiguity for large droplets in the two-detector configuration that is shown in FIGS. 3A-C. For instance, large particles yield not only a phase shift but also a time shift of the entire signal, which is related to the measurement volume displacement. The software in the CPU 18 can use this time shift to determine the correct multiple of $2\pi$ to be used.

Figure 4:
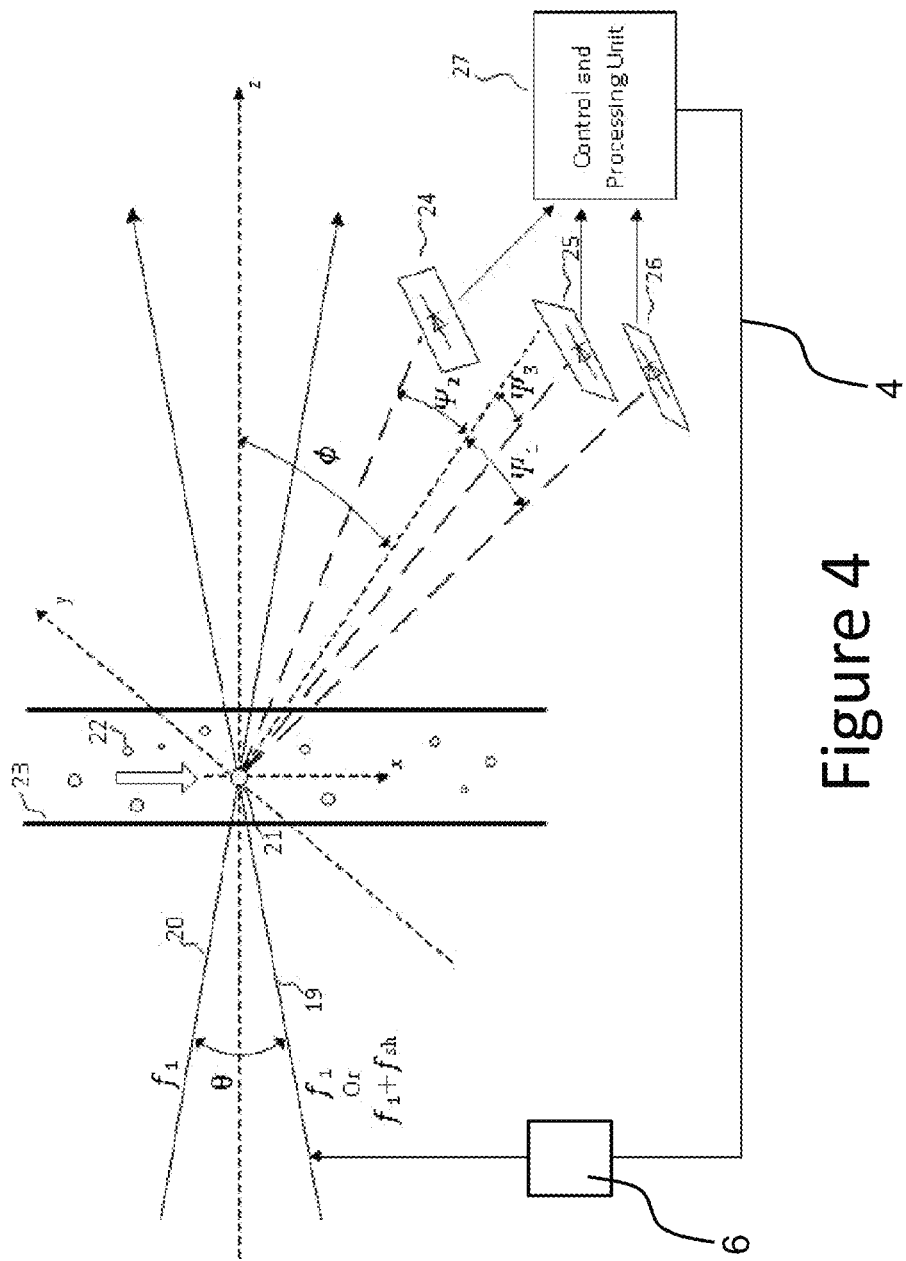
FIG. 4 is a simplified diagram illustrating a dual beam optical system for measuring Steam Quality in a steam conduit utilizing Laser Doppler Velecomietery and Phase Doppler Anemometry techniques in a three-detector configuration.

FIG. 4 is a simplified diagram showing a system according to an embodiment, with a three-detector configuration employing Phase Doppler Anemometry (PDA) and Laser Doppler Velocimetry (LDV) techniques. The three-detector configuration overcomes the $2\pi$ ambiguity that is associated with the two-detector configuration described above with reference to FIG. 3. Steam flows in a steam conduit 23 and droplets of water liquid 22 are present in the steam. Two coherent light beams 19, 20 with the same polarization of the same frequency $\lambda_1 = f_1$ converge on the measurement volume 21 with an intersection angle of $\Theta$. Optionally, one of the two coherent light beams 19, 20 has a frequency shift $f_{sh}$. In this configuration, the detectors 24, 25, 26 cooperate to measure three phase-differences. The droplet diameter $d_d$ is calculated similarly as in equation (6), but now the third phase measurement difference can be used as a validation criteria because equation (9) must be satisfied;

$$\Delta\varphi_{r,12} = \Delta\varphi_{r,13} - \Delta\varphi_{r,23} \quad (9)$$

Utilizing equations (6) and (9) the $2\pi$ ambiguity can be overcome for droplets up to a diameter of maximum $d_{dmax}$ for first order refraction, as given by equation (10).

$$d_{dmax} \approx \frac{\lambda_1 |\cos\varnothing/2| \sqrt{1 + n_d^2(T,\lambda_1) - 2n_d(T,\lambda_1)|\cos\varnothing/2|}}{n_d(T,\lambda_1)(\psi_1 - \psi_3)\Theta/2} \quad (10)$$

The droplet diameter $d_d$ and droplet velocity $v_{dx}$ are determined using equations (6) and (8), respectively, based on measurements that are obtained using detectors 24 and 26. The CPU 27 is substantially similar to CPU 18, but additionally includes hardware and software components that are required to support the three-detector configuration shown in FIG. 4. Based on the measured data, the CPU 27 sends control signals via feedback path 4 and controller 6 to a not illustrated steam generation unit for controlling the steam quality, e.g. such as by controlling at least one parameter of the steam generation unit based on the control signals.

Figure 5:
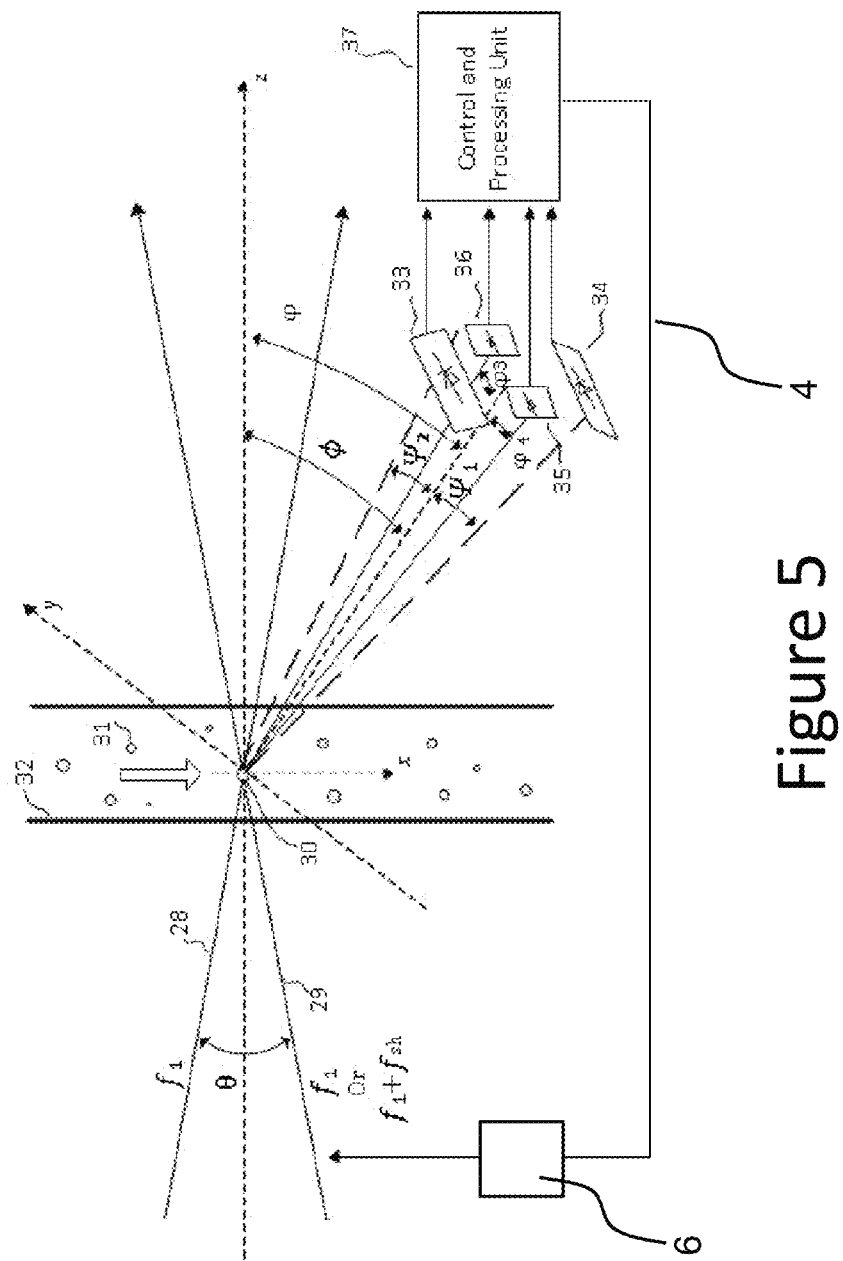
FIG. 5 is a simplified diagram illustrating a dual beam optical system for measuring Steam Quality in a steam conduit utilizing Laser Doppler Velecomietery and Phase Doppler Anemometry techniques in a dual mode configuration with two detectors in a planar configuration.

FIG. 5 is a simplified diagram showing a modified dual-mode form of the two-detector system of FIG. 3. The system that is shown in FIG. 5 overcomes the $2\pi$ ambiguity for large droplets in the two-detector configuration that is shown in FIG. 3. Steam flows in a steam conduit 32 and droplets of water liquid 31 are present in the steam. Two coherent beams of light 28, 29 with the same polarization of the same frequency $\lambda_1 = f_1$ converge on the measurement volume 30 with an intersection angle of $\Theta$. Optionally, one of the two coherent beams of light 28, 29 has a frequency shift $f_{sh}$ relative to the other. In this configuration four detectors are used, two in planar configuration 35, 36 and separated by $\varphi_3$, $\varphi_4$ usually symmetric to the x-z plane about $\varphi$, and two in standard configuration 33, 34 similar to 16, 17 in the system of FIG. 3. In the dual mode technique the $2\pi$ ambiguity is overcome and two velocity components are measured. The planar configuration increases the maximum measurable droplet size, but for small droplets the system may experience oscillations. Therefore for small droplets equation (7) is used in conjunction with measurements obtained using detectors 33, 34 and for large droplets equation (7) is used in conjunction with measurements obtained using detectors 35, 36. The maximum droplet diameter that can be derived depends on the planar configuration detectors 35, 36. Maximum droplet diameter $d_{dmax}$ for first order refraction assuming spherical droplets is given by equation (11).

$$d_{dmax} = 2\pi F_\theta \tag{11}$$

$$= \lambda_1 \left[ \frac{\sqrt{\frac{1+n_d^2(T,\lambda_1)-}{n_d(T,\lambda_1)\sqrt{2}\sqrt{1-\cos(\varphi-\varphi_3-\Theta/2)}}} - }{\sqrt{\frac{1+n_d^2(T,\lambda_1)-}{n_d(T,\lambda_1)\sqrt{2}\sqrt{1-\cos(\varphi-\varphi_3-\Theta/2)}}}} + \frac{\sqrt{\frac{1+n_d^2(T,\lambda_1)-}{n_d(T,\lambda_1)\sqrt{2}\sqrt{1-\cos(\varphi-\varphi_4-\Theta/2)}}}}{\sqrt{\frac{1+n_d^2(T,\lambda_1)-}{n_d(T,\lambda_1)\sqrt{2}\sqrt{1+\cos(\varphi+\varphi_4+\Theta/2)}}}} \right]^{-1}$$

The droplet diameter $d_d$ and droplet velocity $v_{dx}$ are determined using equations (6) and (8), respectively, based on measurements that are obtained using detectors 33 and 34 for small drops, and based on measurements that are obtained using detectors 35 and 36 for large drops. The CPU 37 is substantially similar to CPU 18 or CPU 27, but additionally includes hardware and software components that are required to support the four-detector configuration shown in FIG. 5. Based on the measured data, the CPU 37 sends control signals via feedback path 4 and controller 6 to a not illustrated steam generation unit for controlling the steam quality, e.g. such as by controlling at least one parameter of the steam generation unit based on the control signals.

Optionally the system of FIG. 5 includes three detectors in standard configuration similar to detectors 24, 25 and 26 of FIG. 4.

Figure 6:
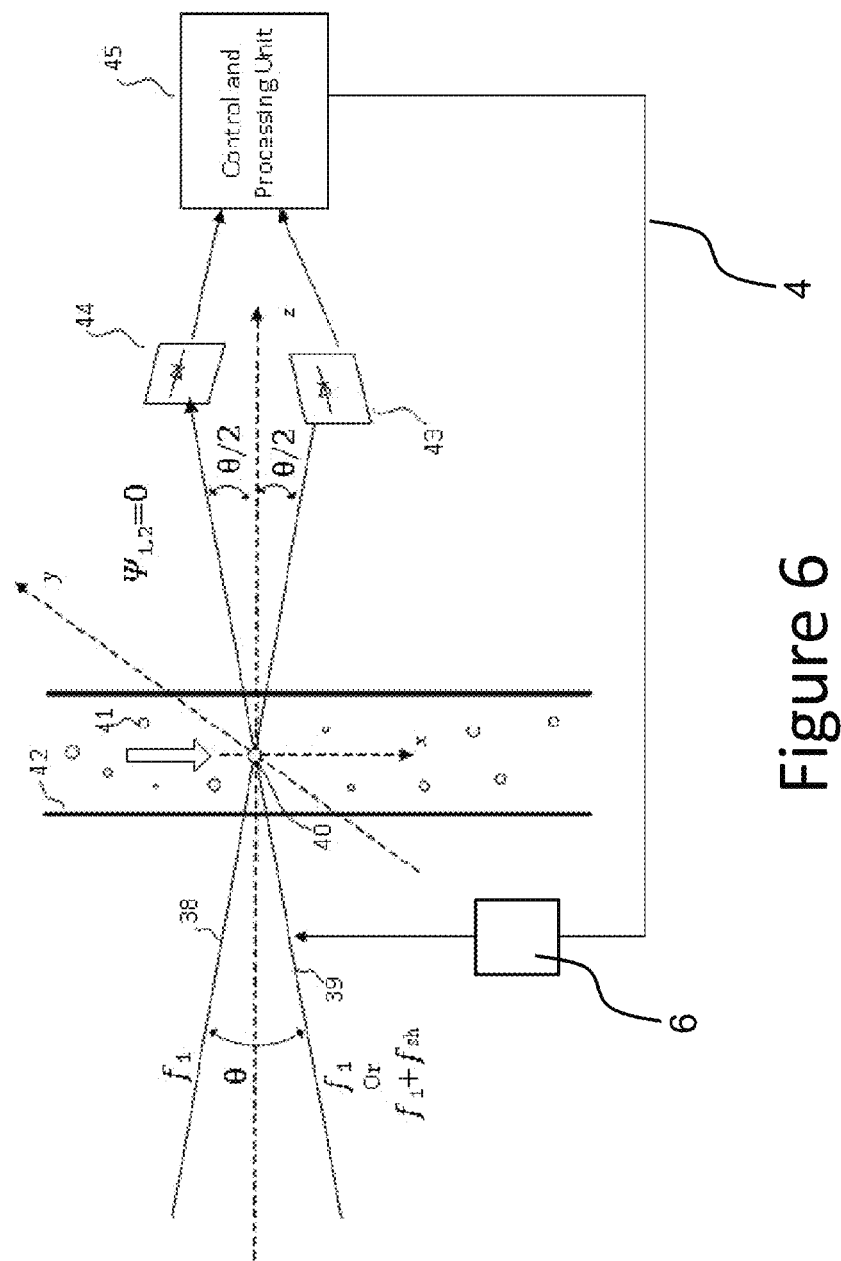
FIG. 6 is a simplified diagram illustrating a dual beam optical system for measuring Steam Quality in a steam conduit utilizing Laser Doppler Velecomietery and Phase Doppler Anemometry techniques in a reference mode configuration.

FIG. 6 is a simplified diagram showing a system according to an embodiment with a reference configuration. Steam flows in a steam conduit 42 and droplets of water liquid 41 are present in the steam. Two coherent light beams 38, 39 with the same polarization of the same frequency $\lambda_1 = f_1$ converge on measurement volume 40 with an intersection angle of $\Theta$. Optionally, one of the two coherent light beams 38, 39 has a frequency shift $f_{sh}$ relative to the other. In the illustrated configuration, at least two detectors 43, 44 are used, each being separated from the y-z plane by $\theta/2$. For first order refraction, detector 44 sees the interference pattern from beam 38 while beam 39 is the reference beam. The scattered wave from beam 38 interferes with the reference beam 39 and the interference pattern of these two beams is detected on 44. Similarly to beam 39. The maxima of the modulated signal are shifted in time, and phase difference between the detectors is a function of the particle diameter. In this configuration the maximum droplet diameter is given by equation (12).

$$d_{dmax} = 2\pi F_\theta \tag{12}$$

$$= \lambda_1 \left[ 2 \left( \sqrt{\frac{1+n_d^2(T,\lambda_1)-}{n_d(T,\lambda_1)\sqrt{2}\sqrt{1+(\cos\Theta/2)^2}}} - \sqrt{\frac{1+n_d^2(T,\lambda_1)-}{n_d(T,\lambda_1)\sqrt{2}\sqrt{1-(\cos\Theta/2^2)}}} \right) \right]^{-1}$$

The droplet diameter $d_d$ and droplet velocity $v_{dx}$ are determined using equations (6) and (8), respectively, based on measurements that are obtained using detectors 43 and 44. The CPU 45 is substantially similar to CPU 18, CPU 27 or CPU 37, but includes hardware and software components that are required to support the two-detector configuration shown in FIG. 6. Based on the measured data, the CPU 45 sends control signals via feedback path 4 and controller 6 to a not illustrated steam generation unit for controlling the steam quality, e.g. such as by controlling at least one parameter of the steam generation unit based on the control signals.

Figure 7:
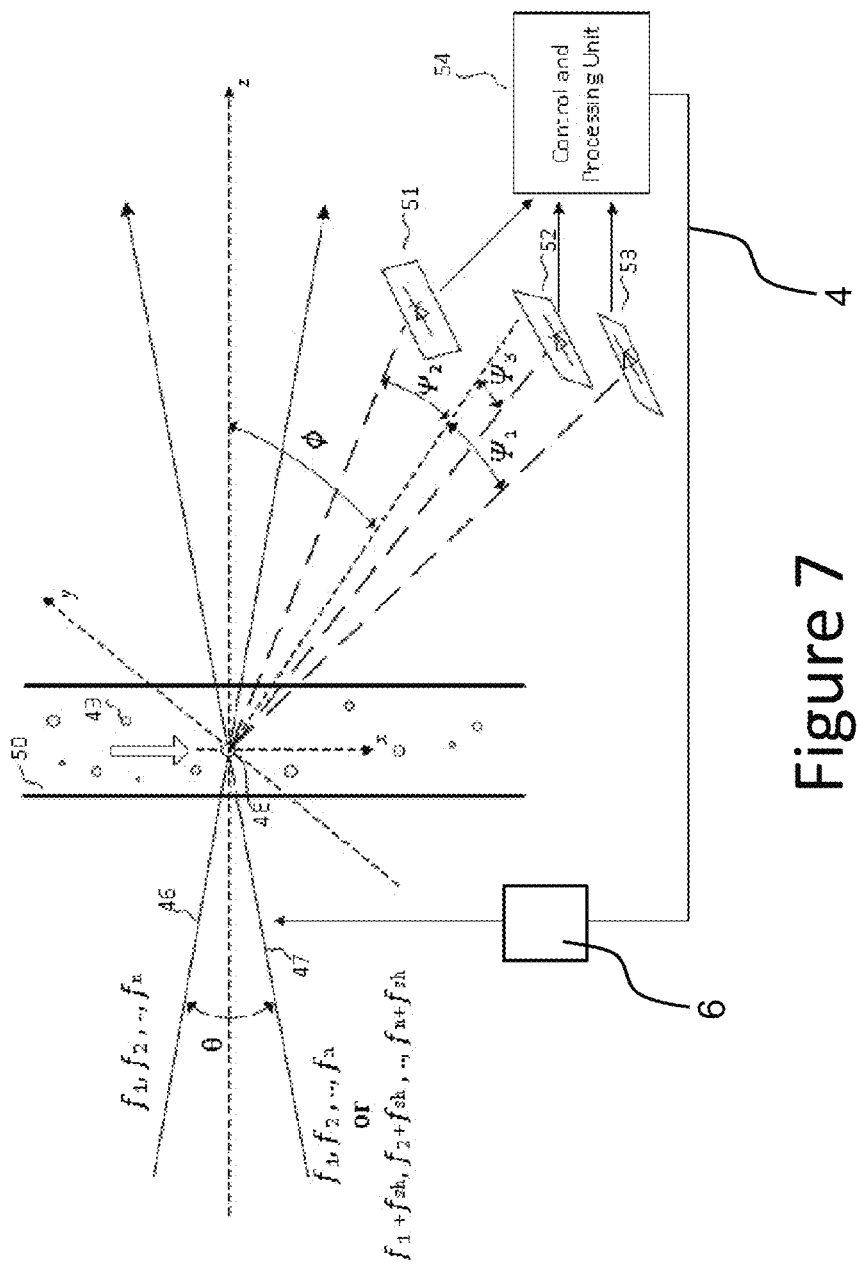
FIG. 7 is a simplified diagram illustrating a dual beam optical system for measuring Steam Quality in a steam conduit utilizing Laser Doppler Velecomietery and Phase Doppler Anemometry techniques in a three-detector configuration with multiple single discrete single wavelength emitters multiplexed. invention.

FIG. 7 is a simplified diagram showing an embodiment in which, rather than using a single wavelength beam, multiple discrete wavelengths are used. Commonly available lasers, diodes or other single wavelength emitters are available in various discrete wavelengths. In this way, wavelengths that are either more or less absorptive to water vapor and wavelengths that are either more or less absorptive to water liquid may be utilized in conjunction with absorption spectroscopy to derive additional data on droplet shape. Until now the discussion and equations shown assumed spherical droplets, but various droplet shapes and deformations may exist in practice. By utilizing multiple discrete wavelengths the decrease in intensity due to absorption can be related to droplet shape using the Beer-Lambert Law (13). The Beer Lambert Law states:

$$\left(\frac{I_t}{I_o}\right)_f = \exp(-k_f L) \qquad (13)$$

where f is the spectrally narrow radiation frequency passing through a medium of length L, $I_t$ is the transmitted light intensity, $I_o$ is the incident light intensity and $k_f$ is the spectral absorption coefficient. The spectral absorption coefficient is related to the imaginary part of the refractive index defined in equation (2), and is shown in equation (14);

$$\text{Im}(n^*) = k(T, \lambda) = \frac{k_f \lambda}{4\pi} \qquad (14)$$

Referring still to FIG. 7, steam flows in a steam conduit 50 and droplets of water liquid 49 are present in the steam. Two coherent light beams 46, 47 with the same polarization and an intersection angle of Θ converge on the measurement volume 48. Multiple discrete wavelengths $f_1, f_2, \ldots, f_n$ are sent through the steam conduit 50 and shifted in time, i.e. only one wavelength is present for a given time interval. In a preferred embodiment wavelengths in the near infrared region are used, including:

at least one wavelength that has high absorption to water vapor and low absorption to water liquid, at least one wavelength that has low absorption to water vapor and high absorption water liquid, and at least one wavelength that has low absorption to water vapor and low absorption to water liquid.

Each wavelength is given a specific period of time for which it will propagate through the system prior to shifting to the next wavelength. The CPU 54 handles shifting from one wavelength to the next, and contains the required multiplexing hardware and synchronization logic, etc. The CPU 54 also controls the $f_{sh}$ shift frequency for each of the respective frequencies for direction velocity measurements. Although FIG. 7 shows a three-detector configuration similar to FIG. 4, in practice any of the other described configurations of detectors may be used. The maximum droplet diameter is given by equation (10), and the phase difference on the detectors is related to the droplet diameter, but in the embodiment of FIG. 7 the intensity of the maxima in the interference patterns will vary depending on the wavelength used. If three frequencies are used $f_1, f_l, f_v$, which $f_1$ is a frequency in which has low absorption in water vapor and water liquid, $f_l$ has high absorption in water liquid and low in water vapor and $f_v$ has high absorption in water vapor and low absorption in water liquid, the relation equation (13) can be approximated by equation (15) for the maxima intensity received on each of the detectors:

$$I_1 = I_v^* \exp(-k_v l_v) = I_l^* \exp(-k_l l_l) \qquad (15)$$

Based on equation (15) the path length of the beams in the vapor portion and path length of which the beam propagates in the liquid droplet can be related to the droplet size and shape in conjunction with the droplet diameter derived using the PDA method. The processing in the CPU accounts for droplet shape and size by the interference spacing, interference intensity maxima and interference frequency to derive the steam quality. For the first order refraction $l_l$ will be the path length which relates to the diameter of the droplet, for first order refraction it will be twice the droplet diameter, and so on for higher order refractions.

Based on the measured data, the CPU 54 sends control signals via feedback path 4 and controller 6 to a not illustrated steam generation unit for controlling the steam quality, e.g. such as by controlling at least one parameter of the steam generation unit based on the control signals.

Numerous other embodiments and variations may be envisaged by a person having ordinary skill in the art without departing from the scope of the invention as defined in the accompanying claims.

The foregoing disclosure and description of the invention is illustrative and explanatory thereof. Various changes in the details of the illustrated structures, construction and method can be made without departing from the true spirit of the invention.

I claim:

1. A system for measuring and controlling steam based on a determination of steam quality, the system comprising:
    a steam conduit comprising: a conduit wall defining an internal volume for containing a steam in a steam system;
    an emitter having a first coherent light beam and a second coherent light beam, each coherent light beam being launched toward a convergence point within said internal volume;
    a receiver for a received signal resulting from interference in space of light from first and second coherent light beams after refraction from a droplet in the steam at the convergence point, the receiver comprising an output port for providing an output signal based on said received signal;
    a processing portion being in communication with said receiver and receiving said output signal from said receiver, said processing portion comprising: processor determining a steam quality value of the steam in the conduit based on the output signal and a control signal based on said steam quality value;
    a controller being in communication with said processor and adjusting a parameter of said steam system based on said control signal; and
    a feedback path being disposed in communication between said processing portion and said controller, said control signal being communicated through said feedback path from said processing portion to said controller.

2. The system of claim 1, wherein the steam flows along a flow direction within the steam conduit, wherein the emitter has an optical axis normal to the flow direction, and wherein an optical path of each of the first and second coherent light beams forms an angle of θ/2 with the optical axis within a first common plane parallel to the flow direction.

3. The system of claim 2, wherein the receiver comprises two receiving elements located off the optical axis and within a second common plane parallel to the flow direction, and wherein the second common plane forms a non-zero angle ϕ with the first common plane.

4. The system of claim 3, wherein the non-zero angle ϕ is between 10° and 60°.

5. The system of claim 3, wherein the two receiving elements are spaced-apart one from the other along the flow direction.

6. The system of claim 5, wherein the receiver further comprises a third receiving element and a fourth receiving element, the third and fourth receiving elements being disposed one each on opposite sides of the second common plane and disposed intermediate the two receiving elements along the flow direction.

7. The system of claim 3, wherein the receiver further comprises a third receiving element located off the optical axis and within the second common plane.

8. The system of claim 3, wherein the two receiving elements and the third receiving element are spaced-apart one from the other along the flow direction, and wherein the third receiving element is disposed between the two receiving elements, and is spaced closer to one of the two receiving element than the other of the two receiving elements.

9. The system of claim 8, wherein the receiver further comprises a fourth receiving element and a fifth receiving element, the fourth and fifth receiving elements being disposed one each on opposite sides of the second common plane and disposed between the third receiving element and the other of the two receiving elements along the flow direction.

10. The system of claim 2, wherein the receiver comprises two receiving elements located off the optical axis and within a second common plane normal to a first common plane, the two receiving elements being disposed one each on opposite sides of the first common plane, one of the two receiving elements being disposed in alignment along the optical path of the first coherent light beam and the other one of the two receiving elements being disposed in alignment along the optical path of the second coherent light beam.

11. The system of claim 1, wherein the emitter is comprised of a source for emitting the first and second coherent light beams with a same polarization of a frequency $f_1$.

12. The system of claim 1 wherein the emitter is comprised of a source for emitting the first and second coherent light beams with a same polarization of a frequency $f_1$ and of a shifted frequency $f_1+f_{sh}$, respectively.

13. The system of claim 1, wherein the emitter is comprised of a source for emitting, in a time sequence order, the first and second coherent light beams with a same polarization of each of a plurality of frequencies $f_1, f_2, \ldots f_n$.

14. The system of claim 1, wherein the emitter is comprised of a source for emitting, in a time sequence order, the first and second coherent light beams with a same polarization of each of a plurality of frequencies $f_1, f_2, \ldots f_n$ and of each of a plurality of shifted frequencies $f_1+f_{sh}, f_2+f_{sh}, \ldots f_n+f_{sh}$.

15. The system of claim 1, wherein the receiver is comprised of an in-line probe, and wherein the two receiving elements are pre-aligned and mounted in the in-line probe.

16. A system for measuring and controlling steam based on a determination of steam quality, the system comprising:
a steam conduit comprising a conduit wall defining an internal volume for containing steam in a steam system;
an optical sensor portion mounted on the steam conduit, said optical sensor portion comprising:
an emitter having a first coherent light beam and a second coherent light beam, each coherent light beam being launched through the internal volume and along respective first and second optical paths, the paths converging with a convergence angle θ, each optical path forming an angle θ/2 with an optical axis of the emitter; and
a receiver comprising at least two receiving elements, each receiving element being in communication with a photosensitive element, the at least two receiving elements located off the optical axis of the emitter and at respective positions along the conduit wall for receiving a signal resulting from interference in space of light from the first and second coherent light beams after refraction from a droplet in the steam, the respective positions of the at least two receiving elements being such that each receiving element receives the signal with a different phase, and the receiver further comprising an output port for providing an output signal based on signals received by the at least two receiving elements;
a processing portion being in communication with said receiver and receiving the output signal from said receiver, said processing portion comprising a processor for determining a steam quality value of the steam based on the output signal and a control signal based on said steam quality value;
a controller being in communication with said processor and adjusting a parameter of the steam system based on said control signal; and
a feedback path being disposed in communication between said processing portion and said controller, said control signal being communicated through said feedback path from said processing portion to said controller.

17. The system of claim 16, wherein the steam flows along a flow direction within the steam conduit and the optical axis is normal to the flow direction.

18. The system of claim 17, wherein the at least two receiving elements are spaced apart from one another along the flow direction.

19. The system of claim 16, wherein the at least two receiving elements consists of only two receiving elements.

20. The system of claim 16, wherein the at least two receiving elements consists of only three receiving elements.

21. The system of claim 16, wherein the emitter is comprised of a source for emitting the first and second coherent light beams with a same polarization of a frequency $f_1$.

22. The system of claim 16, wherein the emitter is comprised of a source for emitting the first and second coherent light beams with a same polarization of a frequency $f_1$ and of a shifted frequency $f_1+f_{sh}$, respectively.

23. The system of claim 16, wherein the emitter is comprised of a source for emitting, in a time sequence order, the first and second coherent light beams with a same polarization of each of a plurality of frequencies $f_1, f_2, \ldots f_n$.

24. The system of claim 16, wherein the emitter is comprised of a source for emitting, in a time sequence order, the first and second coherent light beams with a same polarization of each of a plurality of frequencies $f_1, f_2, \ldots f_n$ and of each of a plurality of shifted frequencies $f_1+f_{sh}, f_2+f_{sh}, \ldots f_n+f_{sh}$.

25. The system of claim 16, wherein said receiver is comprised of an in-line probe, and wherein the two receiving elements are pre-aligned and mounted in the in-line probe.

26. A method for measuring and controlling steam based on a determination of steam quality, the method comprising:
providing a flow of steam within a steam conduit of a steam system;
directing first and second coherent light beams toward a convergence point within the internal volume with an emitter;
detecting an optical signal incident on each one of a plurality of photosensitive elements so as to determine an output signal based on the step of detecting, the optical signal resulting from interference in space of refracted light from the first and second coherent light beams after refraction from a droplet in the steam at the convergence point;

determining a control signal based on the output signal with a processor, the control signal corresponding to a parameter of the steam system;

providing said control signal to a controller of the steam system via a feedback communication path; and controlling the parameter of the steam system with said controller so as to alter a property of steam within the steam conduit.

27. The method of claim 26, wherein the step of determining the control signal comprises: determining a steam quality of the steam within the steam conduit with an optical Doppler methodology; and comparing said steam quality to a predetermined target steam quality.

28. The method of claim 27, wherein the optical Doppler methodology is phase Doppler anemometry.

29. The method of claim 27, wherein the step of determining the steam quality comprises: determining at least one property of the steam selected from the group consisting of: water vapor content, water droplet size, water droplet shape, water droplet velocity and water droplet directional velocity.

30. The method of claim 27, wherein the step of directing the first and second coherent light beams comprises: emitting the first and second coherent light beams by an emitter with a same polarization of a frequency $f_1$.

31. The method of claim 27 wherein the step of directing the first and second coherent light beams comprises: emitting the first and second coherent light beams by an emitter with a same polarization of a frequency $f_1$ and of a shifted frequency $f_1+f_{sh}$, respectively.

32. The method of claim 27, wherein the step of directing the first and second coherent light beams comprises: emitting, in a time sequence order, the first and second coherent light beams by an emitter with the a polarization of each of a plurality of frequencies $f_1, f_2, \ldots f_n$.

33. The method of claim 27 wherein the step of directing the first and second coherent light beams comprises: emitting, in a time sequence order, the first and second coherent light beams by an emitter with a same polarization of each of a plurality of frequencies $f_1, f_2, \ldots f_n$ and of each of a plurality of shifted frequencies $f_1+f_{sh}, f_2+f_{sh}, \ldots f_n+f_{sh}$.

* * * * *